United States Patent [19]

Bartuska et al.

[11] 4,183,366

[45] Jan. 15, 1980

[54] HENNA HAIR COLORING AND/OR CONDITIONING COMPOSITIONS

[75] Inventors: William R. Bartuska; Paul Silverman, both of Skokie, Ill.

[73] Assignee: Helene Curtis Industries, Inc., Chicago, Ill.

[21] Appl. No.: 843,581

[22] Filed: Oct. 19, 1977

[51] Int. Cl.$^2$ ............................................. A45D 7/00
[52] U.S. Cl. ...................................................... 132/7
[58] Field of Search ........................................ 132/7, 5

[56] References Cited

PUBLICATIONS

Hair-Dyes and Hair Dyeing Chemistry and Technique by H. Stanley Redgrove, 1939, pp. 70 and 73.
Sagarin-Cosmetics-1957, pp. 487, 775, 566, and 1062.
Formulation and Function of Cosmetics by Dr. J. Stephan Jellinek, 1970, pp. 124, 319 and 253.

*Primary Examiner*—G. E. McNeill
*Attorney, Agent, or Firm*—Dressler, Goldsmith, Clement, Gordon & Shore, Ltd.

[57] ABSTRACT

Henna-based hair coloring and/or hair conditioning compositions comprising from about 75 to about 95 weight percent of henna powder, from about 1.5 to about 5 weight percent of a non-ionic surface active agent, from about 2.5 to about 15 weight percent of a water soluble polymer and from about 0.5 to about 5 weight percent of a quaternary salt, and improved methods of coloring and/or conditioning hair using henna as the coloring and/or conditioning agent.

14 Claims, No Drawings

HENNA HAIR COLORING AND/OR CONDITIONING COMPOSITIONS

BACKGROUND OF THE INVENTION

Traditionally, henna consists of the dried powdered leaves of the plants *Lawsonia Alba, Lawsonia Spinosa* and *Lawsonia Inemis*. The leaves are picked from the henna shrub, which is found in profusion in Egypt, Tunis Africa, Arabia, Persia, India and other tropical countries. In addition, the so-called "black henna" is derived from the leaves of the woad plant and is used to blend with Lawsonia hennas to produce darker shades of red. There is also "neutral henna" which contains no active dyestuff and is used where conditioning of hair is desired without coloring. Neutral henna is derived from the leaves of the lotus tree.

The use of henna powder to color and condition the hair has been known for at least 2,000 years. The first recorded user of henna as a hair dye was Egyptian Queen Ses, mother of King Teto.

In this country, henna was popular in the 1930's and 1940's to add highlights to the hair before it was acceptable to use more permanent hair dyeing formulations. With the advent of more sophisticated hair coloring preparations which impart softer, more natural hair color and the general acceptance of hair coloring, the use of henna diminished. However, with the current emphasis on natural products, henna-based hair dyeing and conditioning compositions are enjoying heightened popularity.

Henna may be applied to the hair in various forms. Henna may be extracted or mixed with boiling water and poured several times over freshly washed hair; it may be mixed with shampoo; or mixed with hot water, acidified to a pH of about 5.5 and applied to the hair. However, modern commercial preparations are generally powders which are mixed with water, applied to the hair as a slurry, covered with a cap for about 1 hour and then rinsed from the hair. While the currently available henna preparations impart various shades of red to the treated hair and, in addition add body and luster to the treated hair, they have a number of disadvantages. The presently available henna powder preparations have a remarked tendency to coalesce into small balls, forming a lumpy mixture which is difficult to apply uniformly to the hair. Furthermore, the henna slurry is difficult to rinse from the hair. A more serious disadvantage is the difficulty of wet combing henna-treated hair; and, perhaps the most serious disadvantage is that the commercial henna treatments create an extreme static condition in the hair which results in undesirable flyaway hair.

With the aforementioned modern emphasis on "natural" products, there is a need for improved henna-based hair treating compositions which can be employed for either coloring the hair, conditioning the hair or both. The present invention provides such improved henna-based hair coloring and/or conditioning compositions which overcomes all of the above problems encountered with the use of presently available commercial products and thus fulfills the need for improved "natural" hair treating compositions.

SUMMARY OF THE INVENTION

The henna-based hair coloring and/or hair conditioning composition of this invention comprises from about 75 to about 95 weight percent of henna powder, from about 1.5 to about 5 weight percent of a non-ionic surface active agent, from about 2.5 to about 15 weight percent of a water soluble polymer and from about 0.5 to about 5 weight percent of a quaternary salt.

Improved methods of treating hair with henna-based preparations are also provided by the present invention.

DETAILED DESCRIPTION OF THE PREFERRED EMBODIMENTS

The henna-based hair coloring and/or hair conditioning compositions of this invention comprise from about 75 to about 95 weight percent, preferably from about 85 to about 92 weight percent of henna powder, from about 1.5 to about 5 weight percent, preferably about about 2 to about 4 weight percent of a non-ionic surface active agent, from about 2.5 to about 15 weight percent, preferably from about 5 to about 10 weight percent of a water soluble polymer and from about 0.5 to about 5 weight percent, preferably from about 1 to about 3 weight percent of a quaternary salt. In addition, the compositions can include, for example, titanium dioxide and additional conditioning agents, such as Polymer JR 125 sold by Union Carbide, fragrances, and the like. Titanium dioxide serves to lighten and improve the appearance of the composition and also takes up excess oil from oily hair. A suitable range of proportions for titanium dioxide is from about 2.5 to about 8 weight percent.

The henna powder used in the compositions of this invention can be either the color-imparting henna powder or, if only conditioning is desired, the non-color imparting henna powder. In the practice of this invention, the henna composition is mixed with hot tap water, preferably at a temperature of at least 120°–130° F., in a ratio of 1 part powder to about $3\frac{1}{2}$ to $4\frac{1}{2}$ parts of water. The powder and water are mixed to a smooth consistency and applied to freshly shampooed hair. After the application of the henna paste, the hair is covered with a plastic cap to prevent drying and allowed to process for about 1 hours at room temperature, or for a shorter period when heat is added, as by a hair dryer. The paste is then rinsed or shampooed from the hair. It is preferred, in the practice of the method aspect of this invention to additionally rinse the hair with an acid rinse, preferably with a citric acid containing rinse having the pH of from about 2.0 to about 3.5.

The non-ionic surface active agent used in the practice of this invention is preferably one that can be utilized in powder form and can be selected from materials which are available in any form suitable for conversion to powder form. The preferred surface active agents are non-ionic polyethylene oxide-propylene oxide block polymers such as Pluronic F-77, sold by Wyandotte Chemicals Corp., Michigan Alkali Division, Wyandotte, Michigan. The incorporation of the surface active agent eliminates the lumpy consistency encountered with the commercial henna preparations and assists in removing the henna composition from the hair after treatment.

Anionic surface active agents cannot be used in the practice of this invention because they would react with and neutralize the cationic quaternary salt.

The water soluble polymers employed in the practice of this invention are preferably high molecular weight water soluble polymers having amide type linkages similar to the amide linkages of protein, such as polyvinylpyrrolidone K-30 or K-90. It is preferred that the water soluble polymers have a molecular weight of at least 30,000 and more preferably have a molecular weight of at least 300,000. The incorporation of a high molecular weight water soluble polymer having an amide type linkage similar to the amide linkages of protein improves the wet combing properties of henna treated hair and imparts additional body and luster to the hair.

The selection of the quaternary salt employed in the practice of this invention is preferably limited to those compounds which are commonly available as powders, except as discussed hereinbelow, and possess anti-static properties. The preferred quaternary salts which meet the criteria include, for example, lauryl pyridinium chloride, and cetyl pyridinium chloride, and the corresponding bromides.

Illustrative henna powders useful in the practice of this invention include Colora Persian Henna Natural, Colora Persian Henna Brown solid by Color of Canada, Toronto, Canada; Avigal Henna Neutral, Avigal Henna #13 Red, Avigal Henna #13 Black, sold by D-Makrage, New York, and Penick's green henna leaves and brown henna leaves. The neutral or natural colors do not produce any color and thus can be used as conditioning agents alone.

The henna powders are preferably sterilized before being mixed with the other constituents of the compositions of this invention. Sterilization by contact with ethylene oxide gas is preferred.

The following examples further illustrate the compositions and methods of this invention.

EXAMPLE I

A henna composition for normal hair is prepared having the following formulation:

| Ingredient | Weight Percent |
| --- | --- |
| Henna powder | 90 |
| Polyvinylpyrrolidone K-90 | 5 |
| Pluronic F-77 | 3 |
| Lauryl pyridinium chloride | 2 |
| Fragrance | q.s. |

The fragrance is incorporated into the powder, formulation by preparing a 10% slurry of the perfume in henna powder, adding the appropriate amount to the bulk of the formulation and blending thoroughly.

EXAMPLE II

A henna composition for oily hair is prepared having the following formulation:

| Ingredient | Weight Percent |
| --- | --- |
| Henna powder | 85 |
| Polyvinylpyrrolidone K-90 | 5 |
| Pluronic F-77 | 3 |
| Lauryl pyridinium chloride | 2 |
| Titanium dioxide | 5 |
| Fragrance | q.s. |

EXAMPLE III

A henna composition for coarse hair is prepared having the following formulation:

| Ingredient | Weight Percent |
| --- | --- |
| Henna powder | 91 |
| Polyvinylpyrrolidone K-90 | 5 |
| Polymer JR 125 | 2 |
| Cetyl pyridinium chloride | 2 |
| Fragrance | q.s. |

EXAMPLE IV

A henna composition for fine hair is prepared having the following formulation:

| Ingredients | Weight Percent |
| --- | --- |
| Henna powder | 85 |
| Polyvinylpyrrolidone K-90 | 10 |
| Pluronic F-77 | 3 |
| Lauryl pyridinium chloride | 2 |
| Fragrance | q.s. |

EXAMPLE V

An acid rinse composition is prepared having the following formulation:

| Ingredient | Weight Percent |
| --- | --- |
| Citric acid | 2.0 |
| Formalin | 0.1 |
| Water | q.s. to 100 |
| Fragrance | q.s. |

To employ the compositions of this invention, from about 0.5 to about 2 parts, preferably about 1 part, of one of the above compositions, or other compositions falling within the scope of this invention, are mixed with from about $3\frac{1}{2}$ to about $4\frac{1}{2}$ parts of hot tap water to a smooth consistency and applied to freshly shampooed hair. The hair is covered with a cap and allowed to process at room temperature for about one hour, or for shorter periods with added heat. The spent henna slurry is then rinsed and/or shampooed from the hair. It is preferable to additionally rinse the wet, treated hair with a two percent citric acid solution such as the composition set forth in Example V.

Hair treated with the compositions of this invention has more body and luster than untreated hair and holds a set longer than non-henna treated hair.

It will be apparent to one skilled in the art that any henna powder which is capable of imparting color to the hair can be used in the practice of this invention. It will also be apparent to one skilled in the art that any neutral or natural henna powder preparation which does not impart color to the hair can be used for conditioning.

While the preferred surface active agents, water soluble polymers, and quaternary salts have been set forth in the above description of the preferred embodiments, other equivalent agents can be used, even though they are not in powder form, by providing a liquid composition containing the quaternary compound, the water soluble polymer and the surface active agent which can be mixed with henna powder slurry prior to application to the hair.

While the invention has been described with respect to particular embodiments, it will be understood by those skilled in the art that modifications and variations may be employed without departing from the scope of the invention.

We claim:

1. An improved henna composition comprising from about 75 to about 95 weight percent of henna powder, from about 1.5 to about 5 weight percent of a non-ionic surface active agent, from about 2.5 to about 15 weight percent of a water soluble polymer and from about 0.5 to about 5 weight percent of a quaternary salt.

2. The composition of claim 1 wherein said surface active agent is a non-ionic polyethylene oxide-polypropylene oxide block polymer, the water soluble polymer is polyvinylpyrrolidone and the quaternary salt is selected from the group consisting of lauryl pyridinium chloride, cetyl pyridinium chloride, lauryl pyridinium bromide and cetyl pyridinium bromide.

3. The composition of claim 1 wherein said henna powder comprises from about 85 to about 92 weight percent of said composition.

4. The composition of claim 1 wherein said henna powder is a color-imparting henna powder derived from a plant of the genus Lawsonia.

5. The composition of claim 1 wherein said henna powder is a non-color-imparting henna powder derived from the Lotus tree.

6. The composition of claim 1 additionally comprising from about 2.5 to about 8 weight percent of titanium dioxide.

7. A henna based hair coloring composition comprising from about 75 to 95 weight percent of a color-imparting henna powder, from about 1.5 to about 5 weight percent of a non-ionic surface active agent, from about 2.5 to about 15 weight percent of a water soluble polymer and from about 0.5 to about 5 weight percent of a quaternary salt.

8. A henna-based hair conditioning composition comprising from about 75 to about 95 weight percent of a non-color-imparting henna powder from about 1.5 to about 5 weight percent of a non-ionic surface active agent, from about 2.5 to about 15 weight percent of a water soluble polymer and from about 0.5 to about 5 weight percent of a quaternary salt.

9. A method of coloring and conditioning hair comprised from an aqueous slurry of the composition of claim 7, applying said slurry to the hair, maintaining said slurry on the hair for a time period sufficient to impart color thereto, and thereafter rinsing said slurry from the hair.

10. The method of claim 9 comprising the additional step of rinsing the henna-treated hair with an acid rinse.

11. The method of claim 10 wherein said acid rinse is a 2 percent aqueous citric acid solution.

12. A method of improving the condition of hair comprising applying an aqueous slurry of the composition of claim 8 to said hair maintaining the slurry on the hair for a sufficient period of time to impart conditioning thereto, and thereafter rinsing said slurry from the hair.

13. The method of claim 12 comprising the additional step of rinsing said henna treated hair with an acid rinse.

14. The method of claim 13 wherein said acid rinse is a 2 percent citric acid solution.

* * * * *